United States Patent
Abdalla

(10) Patent No.: US 9,174,028 B2
(45) Date of Patent: Nov. 3, 2015

(54) ROUGH BIO-ABSORBABLE STRANDS FOR SEED PLACEMENT

(75) Inventor: Ibrahim Abdalla, Springfield, MO (US)

(73) Assignee: Positive Energy, LLC, Springfield, MO (US)

( * ) Notice: Subject to any disclaimer, the term of this patent is extended or adjusted under 35 U.S.C. 154(b) by 343 days.

(21) Appl. No.: 12/708,303

(22) Filed: Feb. 18, 2010

(65) Prior Publication Data

US 2010/0222627 A1 Sep. 2, 2010

Related U.S. Application Data

(60) Provisional application No. 61/156,845, filed on Mar. 2, 2009.

(51) Int. Cl.
*A61M 36/00* (2006.01)
*A61M 25/04* (2006.01)
*A61N 5/10* (2006.01)

(52) U.S. Cl.
CPC ............. *A61M 25/04* (2013.01); *A61N 5/1027* (2013.01); *A61N 2005/1023* (2013.01)

(58) Field of Classification Search
CPC .............................. A61M 25/04; A61N 5/1027
USPC ...................................................... 600/3, 7, 8
See application file for complete search history.

(56) References Cited

U.S. PATENT DOCUMENTS

| | | | |
|---|---|---|---|
| 5,342,376 A * | 8/1994 | Ruff | 606/151 |
| 5,938,583 A | 8/1999 | Grimm | |
| 6,264,599 B1 | 7/2001 | Slater et al. | |
| 6,264,600 B1 * | 7/2001 | Grimm | 600/7 |
| 6,969,344 B2 * | 11/2005 | Drobnik et al. | 600/3 |
| 7,083,566 B2 * | 8/2006 | Tornes et al. | 600/3 |
| 7,094,198 B2 * | 8/2006 | Terwilliger et al. | 600/3 |
| 7,776,310 B2 | 8/2010 | Kaplan | |
| 2004/0109823 A1 * | 6/2004 | Kaplan | 424/1.11 |
| 2004/0158117 A1 | 8/2004 | Drobnik et al. | |
| 2004/0158118 A1 * | 8/2004 | Drobnik et al. | 600/8 |
| 2007/0021643 A1 * | 1/2007 | Lamoureux et al. | 600/7 |
| 2007/0224237 A1 * | 9/2007 | Hwang et al. | 424/423 |

OTHER PUBLICATIONS

PCT International Search Report and Written Opinion of the International Searching Authority mailed May 7, 2010 regarding International Application No. PCT/US 10/24779, 7 pages.

\* cited by examiner

*Primary Examiner* — John Lacyk
(74) *Attorney, Agent, or Firm* — Shook, Hardy & Bacon, L.L.P.

(57) ABSTRACT

A rough, bio-absorbable strand is provided. More specifically, a bio-absorbable strand having a central body and a rough or irregular outer surface capable of securing the placement of the strand inside a patient is provided. The strand has one or more radioactive seeds embedded in the central body of the strand. The rough outer surface of the strand may include one or more prongs, ridges, strips, grooves, or texture. Additionally, the strand may be capable of being dispensed from an implant needle.

15 Claims, 8 Drawing Sheets

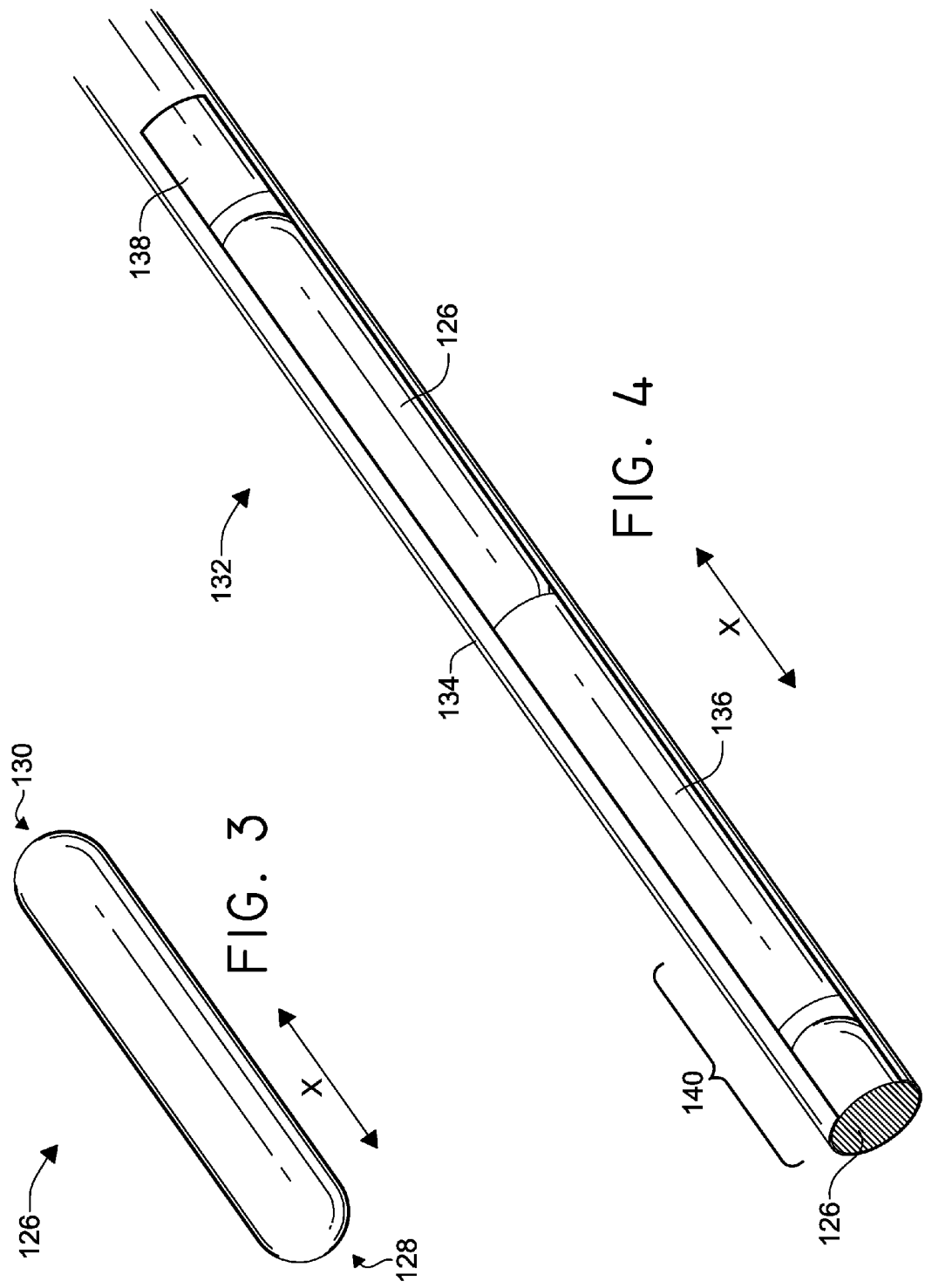

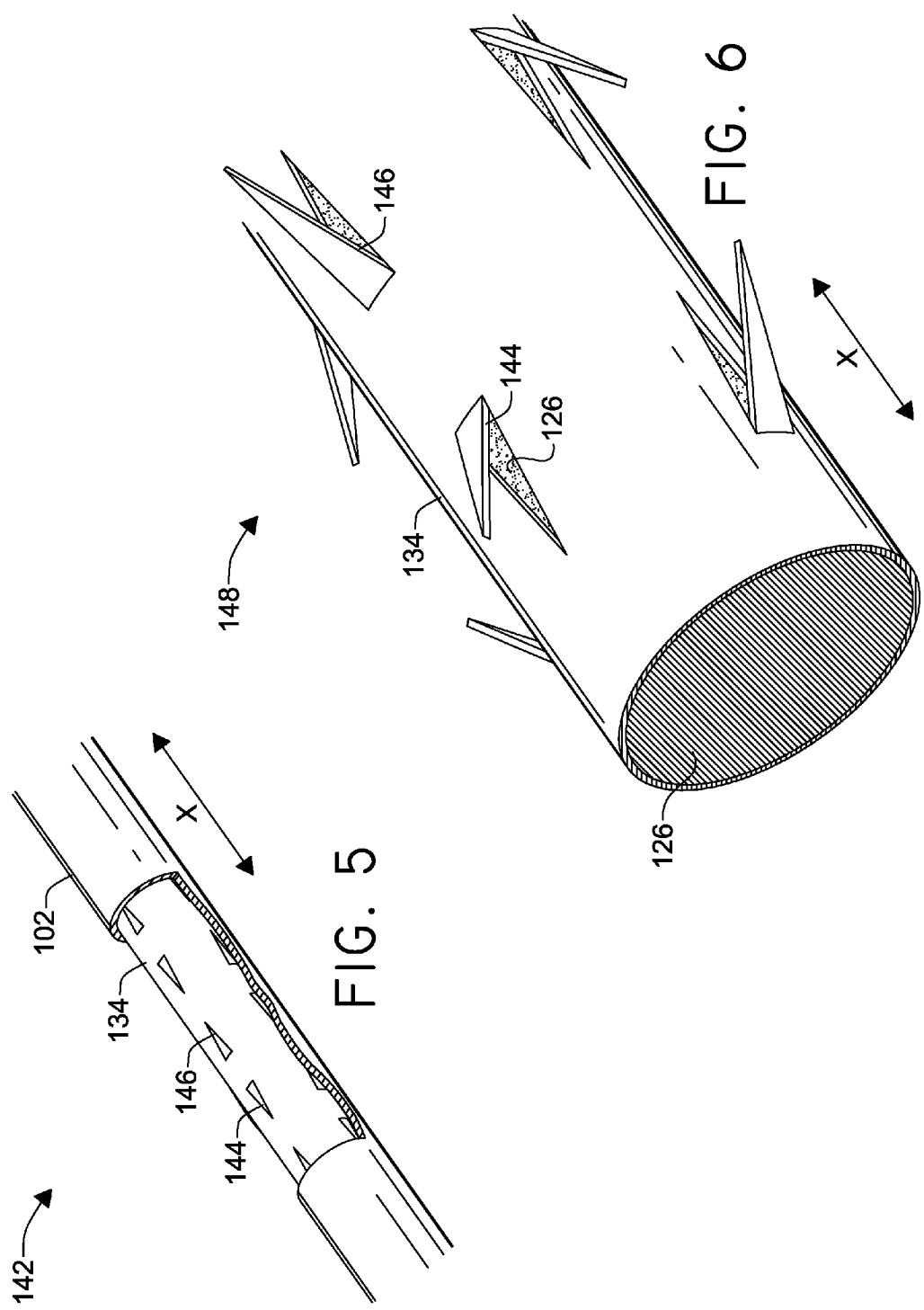

ROUGH BIO-ABSORBABLE STRANDS FOR SEED PLACEMENT

CROSS-REFERENCE TO RELATED APPLICATION

This application claims the benefit of U.S. application 61/156,845, filed Mar. 2, 2009, which is hereby incorporated by reference.

BACKGROUND

Radioactive seed implants are used in the treatment of cancer. Ensuring the proper placement of radioactive seeds enables accurate delivery of treatment and minimizes complications by preventing the seed strands from sliding and shifting away from their intended positions.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter. Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means, instrumentalities and combinations particularly pointed out in the appended claims.

Accordingly, embodiments of the present invention relate to a rough, bio-absorbable strand for securing the placement of radioactive seeds inside a patient. The body of a bio-absorbable strand encloses one or more radioactive seeds and may also enclose spacers for separating the radioactive seeds. The outer surface of the strand is rough or irregular, which enables the strand to be secured inside a patient. Securing a strand inside a patient includes anchoring the strand in place to prevent shifting or movement from the strand's original position. In addition to preventing the strand from shifting within the patient, securing a bio-absorbable strand may also enable more accurate treatment to the intended area of the patient's body.

By way of example only, a rough, bio-absorbable strand's outer surface may include prongs, ridges, grooves, texture, and the like. For instance, a bio-absorbable strand may include one or more prongs projecting from the strand's outer surface. The prongs have the capability to move from a depressed position along the outer surface of a strand when enclosed inside an implant needle, to an extended position projecting from the outer surface of a strand when dispensed from an implant needle. In other instances, a bio-absorbable strand may have ridges or strips of bio-absorbable material on the strand's outer surface. The ridges or strips may be a continuous part of the strand, extending from the strand's surface. Alternatively, the ridges or strips may be additional layers of bio-absorbable material attached to the strand, and may be the same bio-absorbable material as the strand, or a different bio-absorbable material. The ridges or strips may also be wholly or partially connected to the bio-absorbable strand's surface. Still further examples include rough texture or grooves on the surface of the bio-absorbable strand.

Radioactive seeds inside a bio-absorbable strand are separated by spacers. Spacers are placed between the radioactive seeds to prevent excessive radiation doses. In embodiments, spacers may be smooth and cylindrically shaped, and used primarily to separate seeds. In other embodiments, deep grooves in the spacers may help anchor the bio-absorbable strands in place and prevent the strands from sliding and shifting position.

BRIEF DESCRIPTION OF THE DRAWINGS

Embodiments of the present invention are described in detail below with reference to the attached drawing figures that form part of the specification and are to be read in conjunction therewith, and in which like reference numerals are employed to indicate like parts in the various views:

FIG. 3 is a perspective view of an implant seed constructed in accordance with an embodiment of the invention;

FIG. 4 is a perspective view of a bio-absorbable strand constructed in accordance with an embodiment of the invention with a portion of the strand removed to expose seeds and spacers embedded in the body of the strand;

FIG. 5 is a perspective view of the needle body of an implant needle in accordance with an embodiment of the invention with a portion of the needle body removed to expose a rough, bio-absorbable strand;

FIG. 6 is a perspective view of a rough bio-absorbable strand in accordance with an embodiment of the invention;

DETAILED DESCRIPTION

Figure 1:
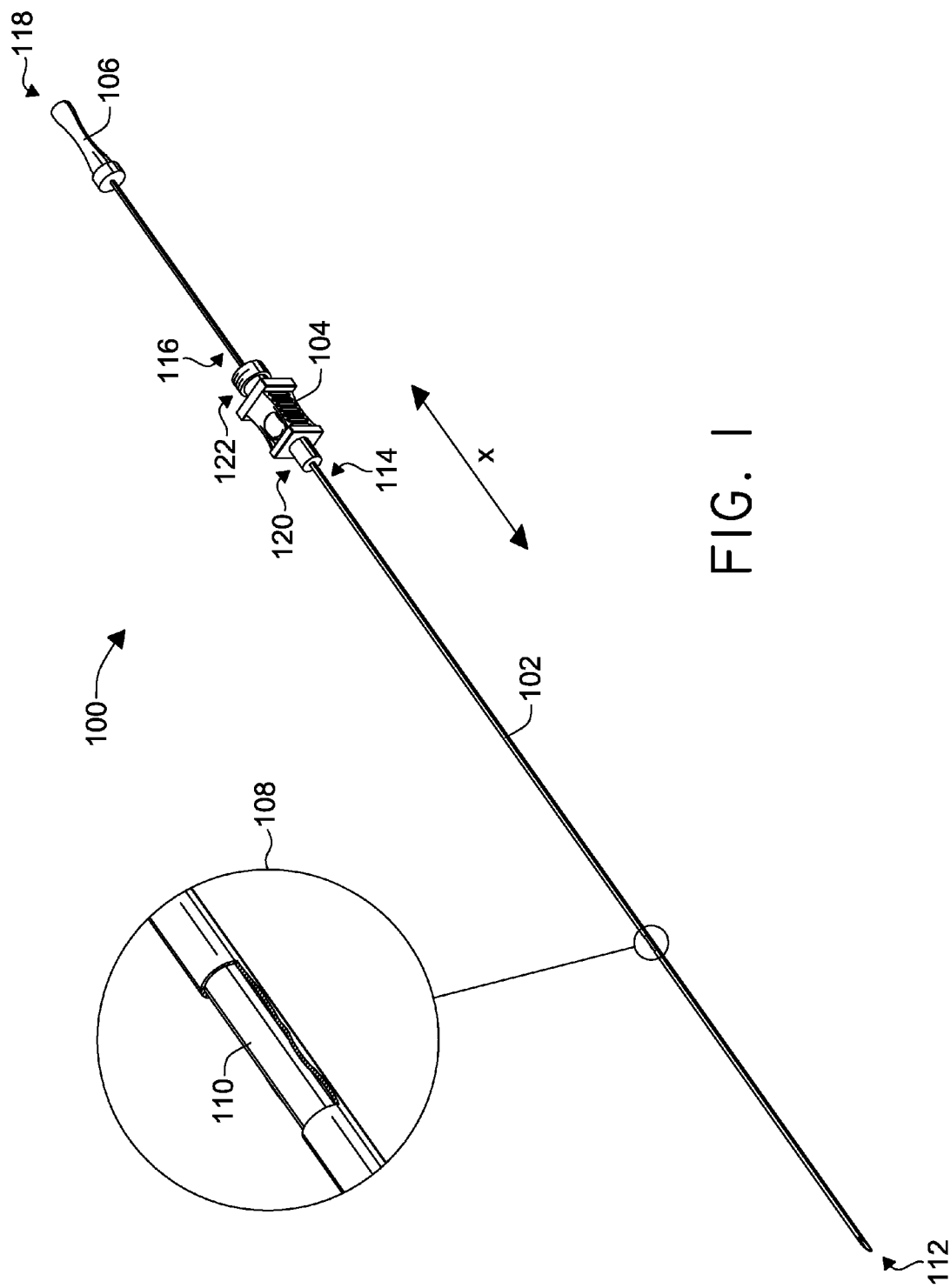
FIG. 1 is a perspective view of an implant needle for placement of a rough bio-absorbable strand constructed in accordance with an embodiment of the invention with an enlarged portion of the needle body removed to expose a strand inside the needle.

Embodiments of the present invention are generally directed to a rough bio-absorbable strand for seed placement. In this regard, a rough bio-absorbable strand is used to secure the placement of radioactive seeds in a patient. The strand comprises a central body of bio-absorbable material defining an internal chamber to receive at least one radioactive seed implanted in the central body of the strand. A bio-absorbable strand, as used herein, refers to one or more than one strand of any material that is capable of being absorbed into the body. By way of example, a bio-absorbable strand may be made of catgut. Catgut refers to a material prepared from animal intestines. However, it will be appreciated that the strand may be made of a variety of bio-absorbable materials including, but not limited to, polymers of polyglycolic acid (polyglycolide) or polylactic acid (polylactide), and other natural or synthetic materials.

The strand further comprises a rough or irregular outer surface on the outside of the central body. To ensure proper placement of a bio-absorbable strand once it is inserted inside a patient, the outer surface of bio-absorbable strands are rough. As used herein, a rough surface refers to any number of variations on the surface of a strand which secures the placement of a strand in a patient. For instance, a rough surface may be an irregular surface. By way of example, and not limitation, a rough surface may be comprised of one or more prongs projecting from the surface of a strand. In other instances, a rough surface may comprise grooves, ridges, or other texture on the surface of the strand. In embodiments, a rough surface may comprise a combination of different kinds of surface variation. As such, a strand may have both prongs and ridges on the surface of the strand. In embodiments, a rough, bio-absorbable strand's outer surface is created by adding an additional rough or irregular treatment to the natural surface of the bio-absorbable strand. Such additional roughness, beyond that which is present by virtue of the natural porosity inherent in bio-absorbable materials, may be accomplished in a variety of ways. A bio-absorbable strand with a rough outer surface may be capable of being dispensed from an implant needle.

The rough surface of a bio-absorbable strand is used to secure the placement of the strand in a patient. As used herein, securing placement of a strand refers to anchoring the strand in place so as to avoid displacement of the strand after insertion into a patient. As such, the likelihood of the strand shifting positions or moving is decreased. Securing the placement of a rough, bio-absorbable strand may also include anchoring the strand in the patient tissue, such that the strand becomes incorporated into the patient's tissue as it is absorbed by the body. In embodiments, securing the placement of a bio-absorbable strand secures the placement of seeds imbedded in the strand, and ensures the subsequent delivery of medical treatment using the strand. A bio-absorbable strand that has shifted may deliver treatment from radioactive seeds to an incorrect area of the body. For example, a bio-absorbable strand may be inserted into a patient for the treatment of prostate cancer. If the strand migrates to the immediate vicinity surrounding the prostate, radiation treatment from the seeds imbedded in the strand may not be delivered as intended. For example, a migrating strand may be less curative by underdosing the cancer and cause more complications by overdosing the surrounding normal structures, such as the rectum and the bladder. It should be understood that rough, bio-bsorbable strands may be inserted into any area of a patient's body where treatment by radioactive seeds is desired. By way of example, and not limitation, strands may be implanted in the breast, lungs, brain, outer extremities, and any other area of the body where strands may be used to accurately deliver radiation treatment.

In embodiments, one or more active elements are imbedded in a bio-absorbable strand. The active elements may have therapeutic properties for treatment of a patient, such as, for example, pharmaceutical, nuclear, or radioactive properties, etc. As such, an active element may be one or more radioactive seeds.

Accordingly, in one aspect, an embodiment of the present invention is directed to a bio-absorbable strand for securing the placement of radioactive seeds inside a patient. The strand comprises an elongated body of bio-absorbable material with a rough outer surface, wherein the rough outer surface is capable of securing the strand inside the patient. The strand further comprises one or more radioactive seeds imbedded in the body of the strand.

In another embodiment, an aspect of the invention is directed to a rough bio-absorbable structure. The structure comprises a central body of bio-absorbable material. The structure further comprises a rough outer surface of the central body, wherein the rough outer surface is made more rough than the natural roughness inherent in the properties of the bio-absorbable material, and is capable of securing the placement of the bio-absorbable structure inside a patient. The structure also comprises one or more radioactive seeds implanted in the central body of the bio-absorbable structure.

A further embodiment of the present invention is directed to a method of making an anchored, bio-absorbable strand for placing radioactive seeds. The method includes creating a strand of bio-absorbable material with central body and a rough outer surface, wherein the strand is capable of being dispensed from an implant needle and the rough outer surface is capable of securing the strand inside a patient. The method further includes embedding one or more radioactive seeds within the body of the strand of bio-absorbable material.

Figure 2:
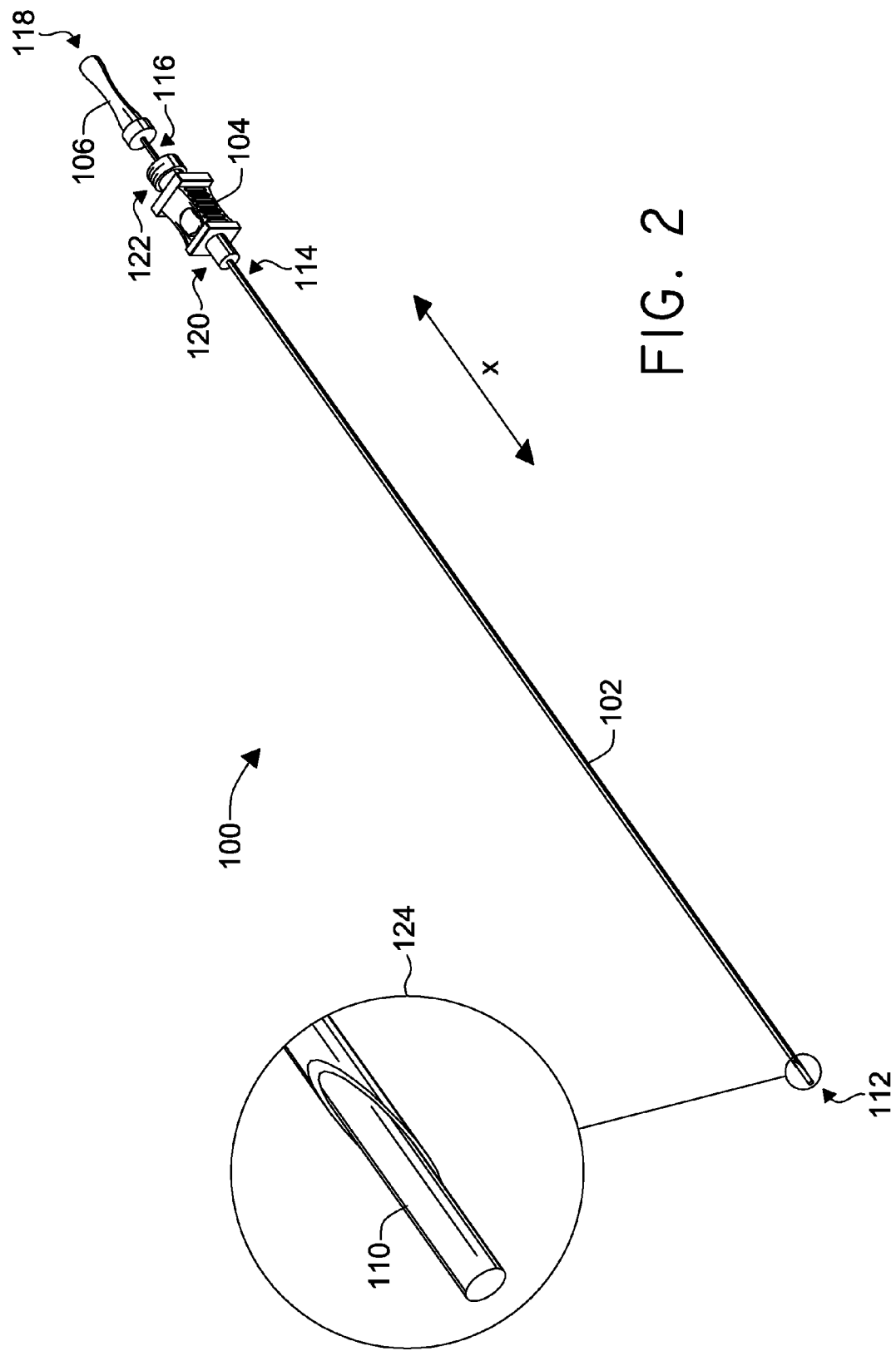
FIG. 2 is a perspective view of an implant needle for placement of a rough bio-absorbable strand constructed in accordance with an embodiment of the invention with the tip of the needle body enlarged.

Having briefly described an overview of embodiments of the present invention, exemplary figures depicting embodiments of the present invention are described below in order to provide a general context for various aspects of the present invention. With reference to FIG. 1 and FIG. 2 in particular, where like reference numerals identify like elements in the various views, an exemplary implant needle is illustrated and designated generally by the numeral 100. Implant needle 100 generally includes needle body 102, needle hub 104, and stylet 106. As illustrated, needle body 102 is an elongated cylinder with an internal chamber and a central longitudinal axis "x." Needle body 102 is generally hollow in shape and includes axially opposed first and second ends. The proximal first end 112 is open and inserted into a patient, while distal second end 114 is contained within needle hub 104. Needle body 102 has an internal diameter capable of receiving stlyet 106 through needle hub 104. Needle body 102 may have an inner diameter of about 0.838 millimeters. In embodiments, needle body 102 has an inner diameter in the range of about 0.241 to 2.691 millimeters.

Stylet 106 is an elongated cylinder along the central longitudinal axis of needle body 102. Stylet 106 includes axially opposed first and second ends. The proximal first end 116 is inserted into needle body 101 through needle hub 104, and the distal second end 118 remains exposed. Upon depression, stylet 106 is received by needle body 102 and inserted through needle hub 104. In embodiments, inserting stylet 106 into needle body 102 advances or dispenses the contents of needle body 102 into a patient.

Needle hub 104 is positioned along the central longitudinal axis of needle body 102. Needle hub 104 includes axially opposed first and second ends. The proximal first end 120 of needle hub 104 encloses the distal end 114 of needle body 102. The distal second end 122 of needle hub 104 is open, and receives the proximal first end 116 of stylet 106.

Enlargement 108 depicts a cut away portion of needle body 102, revealing strand 110. Strand 110 is contained within the internal chamber, and positioned along the central longitudinal axis, of needle body 102. Strand 110 may be a rough bio-absorbable strand embedded with radioactive seeds. Although depicted as being cylindrical in shape, it will be appreciated that strand 110 may include a non-cylindrical body of rough, bio-absorbable material for being inserted into a patient. For example, strand 110 may have a circular, triangular, or square-shaped cross-section. In embodiments, implant needle 100 is used to insert strand 110 into a patient. By way of example, stylet 106 is inserted through needle hub 104 to dispense strand 110 out of the proximal first end 112 of needle body 102 and into a patient.

As illustrated in FIG. 2, enlargement 124 depicts strand 110 advancing out of the proximal first end 112 of needle body 102 and into a patient. Additionally, stylet 106 is shown as having been inserted through needle hub 104 into needle body 102, such that strand 110 is being advanced and out of the proximal first end 112 of needle body 102, and distal second end 118 of stylet 106 is depressed through needle hub 104.

With reference now to FIG. 3, an exemplary implant seed 126 is shown for embedding within a rough, bio-absorbable strand. Implant seed 126 is generally cylindrical in shape along a central, longitudinal axis "x." Implant seed 126 includes axially opposed first and second ends. Proximal first end 128 and distal second end 130 are closed. In embodiments, implant seed 126 has an approximate diameter of about 0.8 millimeters and an approximate length of about 4.5 millimeters. It should be understood that, depending on the location and size of the area inside a patient that is being treated, any diameter and length of an implant seed may be used. For example, an implant seed may have an inner diameter in a range between about 0.23 and 2.68 millimeters and a length between a range of about 10 to 150 millimeters. In some instances, an implant seed used to treat cancer in outer extremities may be as long as needed for the intended treatment area.

As used herein, a seed is any seed used to deliver treatment to a patient. The treatment may be chemical, radiation, nuclear, biological, etc. The term "seed" or "seeds" may be used to refer to one or more than one seed. Implant seed 126 may be implanted in a patient for delivery of treatment. More specifically, implant seed 126 may be imbedded in the body of a rough, bio-absorbable strand that is implanted in a patient. More than one implant seed 126 may be imbedded within a single rough, bio-absorbable strand. Implant seed 126 may be, or may later become, radioactive. As such, a radioactive seed functions to deliver radiation treatment to a patient when imbedded in a bio-absorbable strand an inserted in a patient. It should be understood that the number of radioactive seeds may vary between different strands of rough, bio-absorbable material depending on the intended patient for which the strand is created. For example, to deliver a higher dose of treatment to a patient, more than one radioactive implant seed 126 may be used. In some instances, implant seed 126 is used for patient treatment during brachytherapy. As part of such treatment, delivery of specific doses of radiation to specific parts of a patient's body may be directed through the placement of rough, bio-absorbable strands of one or more implant seed 126.

With reference to FIGS. 4-12, exemplary rough, bio-absorbable strands in accordance with various embodiments of the present invention are shown, with like reference numerals identifying like elements. It will be understood and appreciated by those of ordinary skill in the art that FIGS. 4-12 are provided by way of example only and are not intended to limit the scope of the present invention in any way.

Referring initially to FIG. 4, an illustrative rough bio-absorbable strand 132 used for seed placement is shown. As shown in FIG. 4, strand 132 generally includes outer surface 134, radioactive seed 126, and spacers 136 and 138. Strand 132 also includes area 140 depicting a cut away portion of outer surface 134, which reveals the contents inside strand 132. The body of strand 132 is generally cylindrical in shape and is positioned along a central, longitudinal axis "x." It should be understood that the cylindrical shape of strand 132 may vary between embodiments, and that the shape of strand 132 is such that at least one seed 126 may be embedded inside or contained within hollow strand 132. As used herein, a spacer refers to one or more segments of bio-absorbable material. For example, spacers may be non-radioactive segments of bio-absorbable material placed between radioactive seeds to prevent excessive doses. In embodiments, one or more spacers are used to separate more than one seed 126. For instance, two radioactive seeds may be separated by five spacers. In embodiments, spacers 136 and 138 may be made of the same bio-absorbable material as the outer surface 134 of strand 132. In other instances, spacers 136 and 138 may be a different bio-absorbable material than strand 132 or may be natural or synthetic materials. Spacers may have a smooth, cylindrical outer surface. Alternatively, spacers may have deep grooves in the outer surface of the spacer. In embodiments, grooves in the outer surface of the spacers are used to prevent bio-absorbable strands from sliding and shifting.

In embodiments, strand 132 has an inner diameter of about 0.838 millimeters when used in an 18-guage needle. In other embodiments, strand 132 has an inner diameter in the range of about 0.241 to 2.691 millimeters for a needle between about 26-guage to 10-guage, respectively. As explained with reference to FIG. 3, seed 126 may have a diameter of about 0.8 millimeters. In embodiments, the inner diameter of seed 126 is within the range of about 0.23 to 2.68 millimeters. Therefore, the bio-absorbable material of strand 132 surrounding seed 126 may have a thickness of about 0.019 millimeters. In further embodiments, spacers 136 and 138 may have the same or different diameter as seed 126. For example, spacers 136 and 138 may be about 0.8 millimeters thick. In embodiments, bio-absorbable strand 132 is capable of being dispensed from an implant needle 100 with an inner diameter of 0.838 millimeters in needle body 102, as depicted in FIGS. 1 and 2.

Referring to FIG. 5, an illustrative rough, bio-absorbable strand 142 is shown, enclosed by needle body 102, with a portion of needle body 102 removed. Rough, bio-absorbable strand 142 generally includes strand surface 134 and prongs 144 and 146, inside needle body 102. Rough, bio-absorbable strand 142 is cylindrical in shape and positioned along a central, longitudinal axis "x." In embodiments, when enclosed in needle body 102, prongs 144 and 146 are depressed along the surface of bio-absorbable strand 142. Further, when dispensed from needle body 102, prongs 144 and 146 may project or extend from the surface of strand 142 as shown in FIG. 6. As such, prongs 144 and 146 function to anchor or secure the placement of strand 142 when inserted in a patient. It should be understood that prongs 144 and 146 are one embodiment of a type of rough texture on the surface of bio-absorbable strand 142. For example, other types of surface treatment, including ridges, strips, grooves, or other texture, may also create a rough surface on bio-absorbable strand 142. As explained with reference to FIGS. 1 and 2, rough, bio-absorbable strand 142 may be enclosed inside needle body 102 of an implant needle 100. Further, rough, bio-absorbable strand 142 may be capable of being dispensed out the proximal open end 112 of needle body 102 and into a patient.

With reference now to FIG. 6, an illustrative rough, bio-absorbable strand 148 is shown. Strand 148 is cylindrical in shape and has a central longitudinal axis "x." As show in FIG. 6, strand 148 generally includes strand surface 134, prongs 144 and 146, and seed 126. As depicted previously in FIG. 5, prongs 144 and 146 remain depressed when enclosed inside the needle body 102 of an implant needle 100. As shown in FIG. 6, prongs 144 and 146 project outward from strand surface 134 of a rough, bio-absorbable strand 148, when advanced out of or dispensed from an implant needle 100. Strand 148 may include any number of prongs 144 and 146 positioned along the central longitudinal axis of strand 148. It should be understood that prongs 144 and 146 may project in any direction from strand surface 134. For example, prongs 144 and 146 may point in opposite directions from each other.

In embodiments, strand 148 is capable of being dispensed from needle body 102 of an implant needle 100, as depicted in FIGS. 1 and 2.

Figure 7:
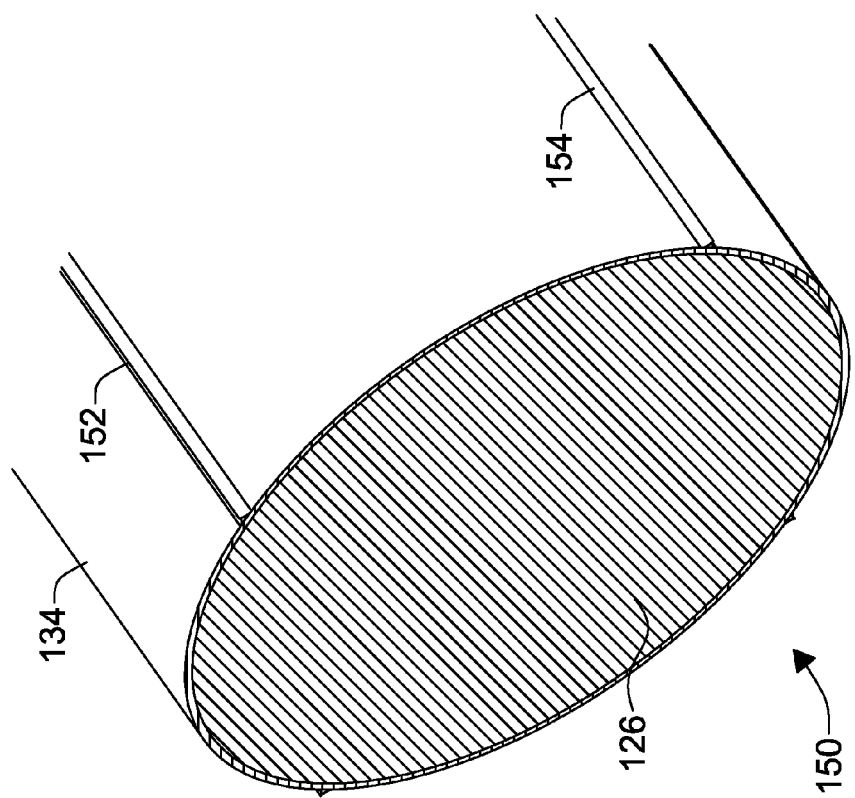

Referring to FIG. 7, an illustrative cross-sectional view of rough bio-absorbable strand 150 is shown. FIG. 7 illustrates strand surface 134, ridges 152 and 154, and seed 126. The body of strand 150 is cylindrical in shape and positioned along a longitudinal axis. In embodiments, ridges 152 and 154 extend lengthwise along the body of strand 150. Ridges 152 and 154 may be varied in thickness. In embodiments, ridges 152 and 154 are 0.01 millimeters thick. Strand surface 134 may include any number of ridges, and the ridges may be varying thicknesses. Ridges 152 and 154 may be a continuous part of strand surface 134, or may be additional, attached layers of bio-absorbable material on top of strand surface 134. As such, ridges 152 and 154 may be the same bio-absorbable material as strand 150, or may be a different bio-absorbable material. In embodiments, strand 150 is capable of being dispensed from needle body 102 of an implant needle 100, as depicted in FIGS. 1 and 2.

Ridges 152 and 154 may be fully or partially connected to strand surface 134. For example, ridges 152 and 154 may be a continuous part of strand surface 134 in parts, and may split off of strand surface 134 in other parts. Alternatively, ridges 152 and 154 may be additional layers of bio-absorbable material that are attached in some parts and split off from other parts of strand surface 134. As previously depicted by FIG. 6, in which prongs 144 and 146 projected from strand surface 134, ridges 152 and 154 may project from strand surface 134 where not fully connected. Similarly, as depicted by FIG. 5, in which prongs 144 and 146 were depressed along the surface of bio-absorbable strand 142, ridges 152 and 154 may also remain depressed along surface 134 of strand 150 when enclosed in the needle body 102 of an implant needle 100. In embodiments, split-off portions of ridges 152 and 154 may help anchor the placement of bio-absorbable strand 150.

Figure 8:
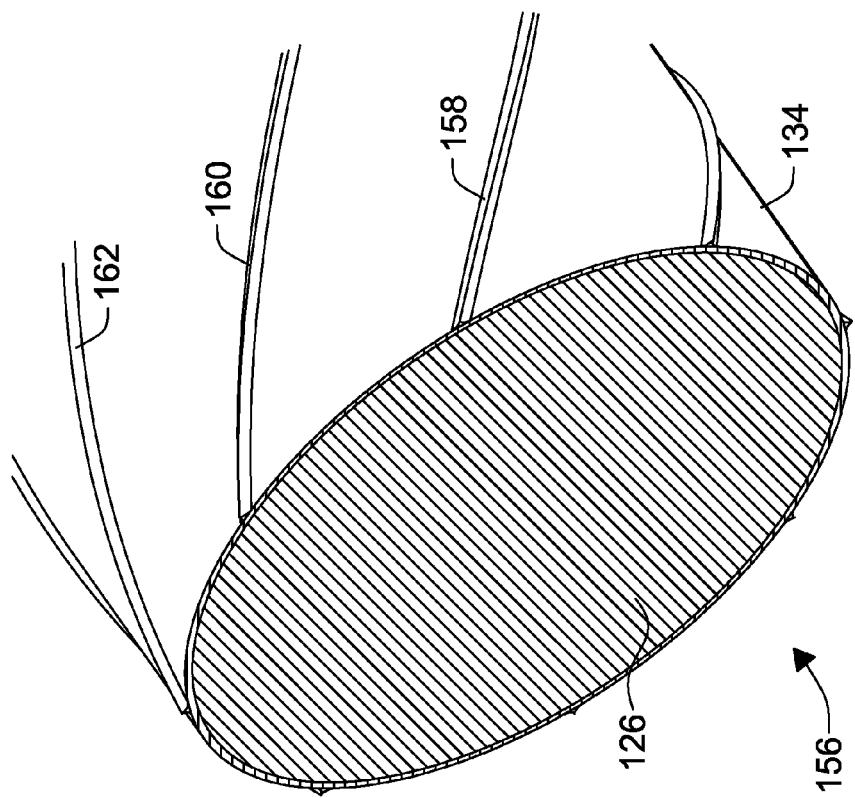
FIGS. 7-12 are perspective views of rough bio-absorbable strands in accordance with embodiments of the invention.

With reference now to FIG. 8, an illustrative cross-sectional view of rough, bio-absorbable strand 156 is shown. Strand 156 generally includes strand surface 134, ridges 158, 160, and 162, and seed 126. The body of strand 156 is cylindrical in shape and positioned along a longitudinal axis. It should be understood that strand surface 134 may include any number of ridges 158, 160, and 162. Ridges 158, 160, and 162 may be rotationally positioned along strand surface 134. For example, ridges 158, 160, and 162 may be rotationally positioned in a corkscrew manner along the body of strand 156. In embodiments, ridges 158, 160, and 162 are a continuous part of strand 156, extending from strand surface 134. In other embodiments, ridges 158, 160, and 162 are additional, attached layers of bio-absorbable material attached on top of strand surface 134. Ridges 158, 160, and 162 may be the same bio-absorbable material as strand 156, or may be a different bio-absorbable material. Further, ridges 158, 160, and 162 may be fully or partially connected to strand surface 134. Where partially connected, ridges 158, 160, and 162 may help anchor the placement of bio-absorbable strand 156 in a patient. Strand 156 may be capable of being dispensed from needle body 102 of an implant needle 100, as depicted in FIGS. 1 and 2.

Figure 9:
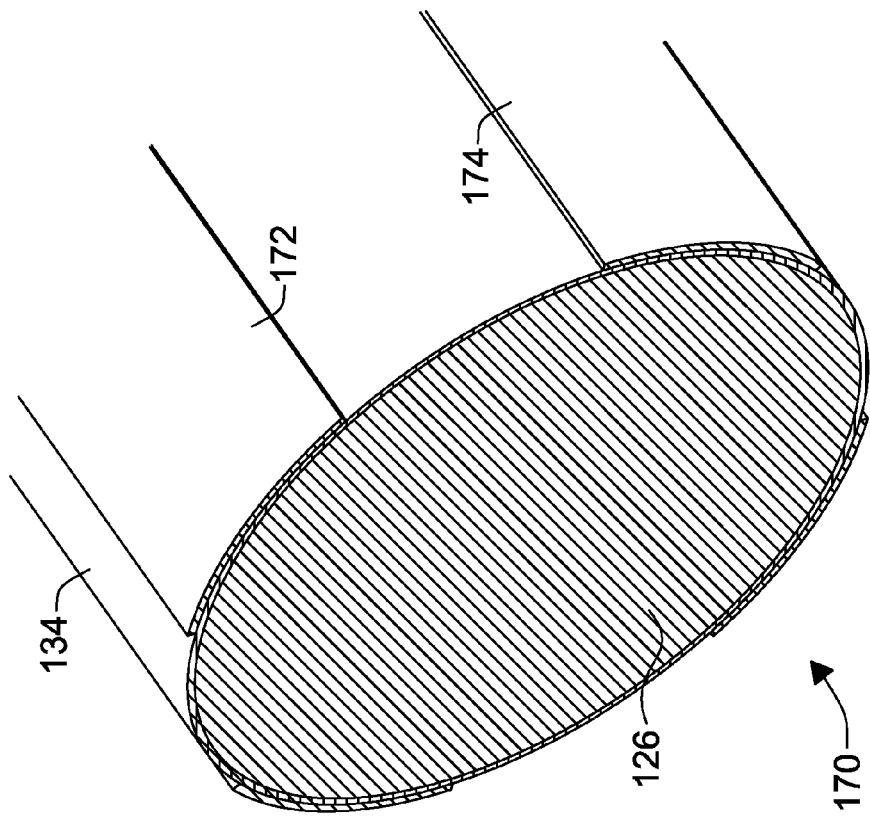

Referring next to FIG. 9, an illustrative cross-sectional view of rough bio-absorbable strand 164 is shown. FIG. 9 illustrates strand surface 134, strips 166 and 168, and seed 126. The body of strand 164 is cylindrical in shape and positioned along a longitudinal axis. Strips 166 and 168 may overlap. Strand surface 134 may contain any number of strips which can vary in thickness and width. In embodiments, strips 166 and 168 are 0.01 millimeters thick. As discussed with reference to FIG. 8, strips 166 and 168 may be continuous parts of strand 164, extending from strand surface 134, or may be additional, attached layers of bio-absorbable material. Strips 166 and 168 may be the same bio-absorbable material as strand 164, or may be a different bio-absorbable material. In embodiments, strips 166 and 168 may be fully or partially attached to strand surface 902. Strand 164 may be capable of being dispensed from needle body 102 of an implant needle 100, as depicted in FIGS. 1 and 2.

Figure 10:
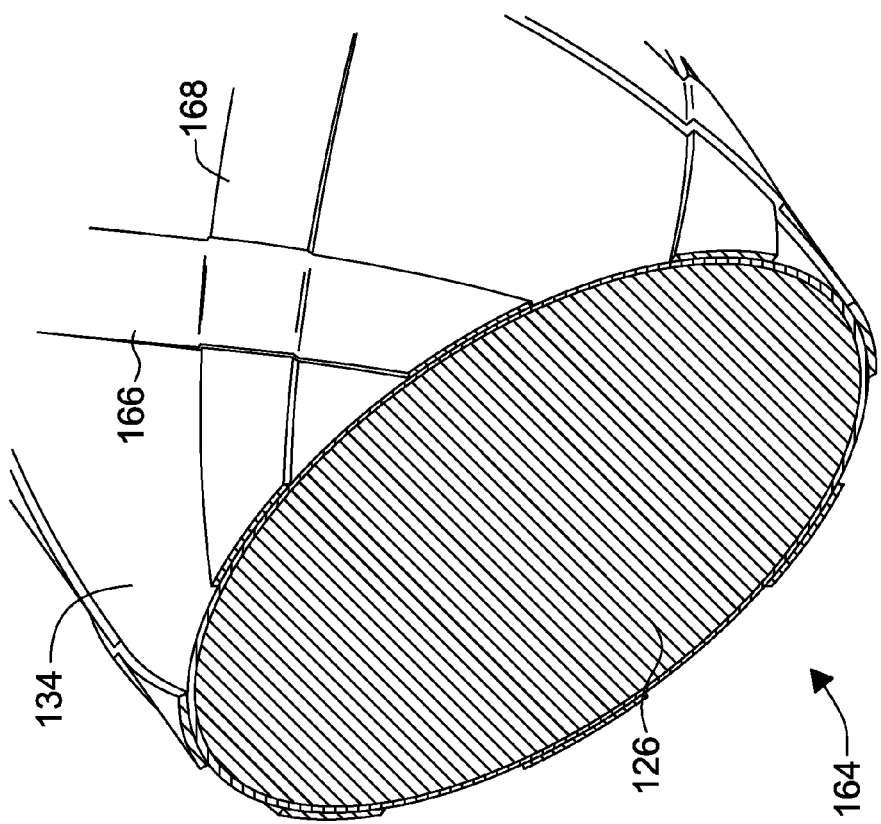

With reference to FIG. 10, an illustrative cross-sectional view of rough bio-absorbable strand 170 is shown. FIG. 10 illustrates strand surface 134, strips 172 and 174, and seed 126. The body of strand 170 is cylindrical in shape and positioned along a longitudinal axis. Strand surface 134 may include any number of strips which can vary in thickness and width. In embodiments, strips 172 and 174 are 0.01 millimeters thick. As discussed with reference to FIG. 8, strips 172 and 174 may be continuous parts of strand 170, extending from strand surface 134, or may be additional, attached layers of bio-absorbable material. Strips 172 and 174 may be the same bio-absorbable material as strand 170, or may be a different bio-absorbable material. In embodiments, strips 172 and 174 may be fully or partially attached to strand surface 134. Strand 170 may be capable of being dispensed from needle body 102 of an implant needle 100, as depicted in FIGS. 1 and 2.

Figure 11:
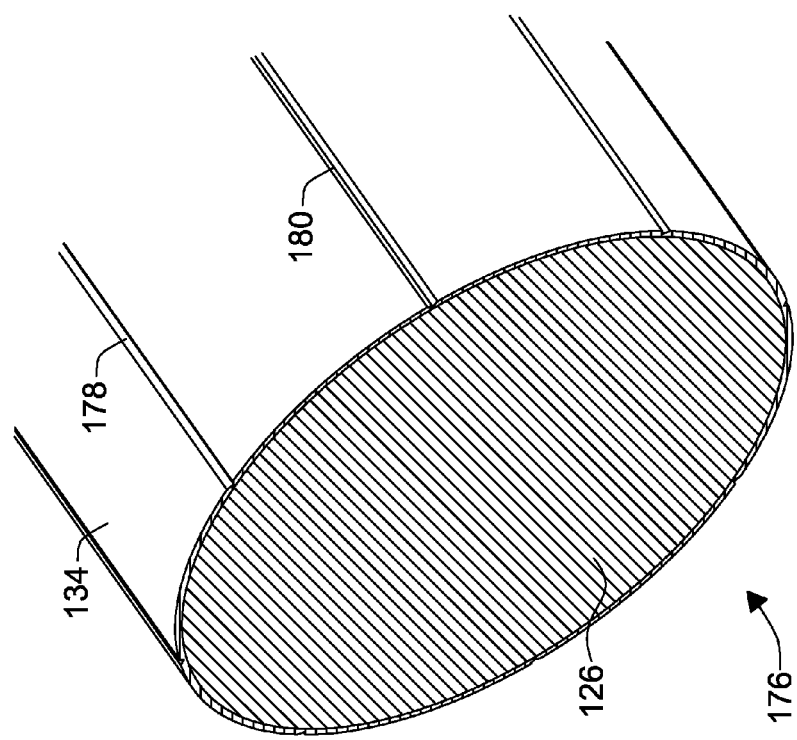

Referring to FIG. 11, an illustrative cross-sectional view of rough bio-absorbable strand 176 is shown. FIG. 11 illustrates strand surface 134, grooves 178 and 180, and seed cross-section 140. The body of strand 170 is cylindrical in shape and positioned along a longitudinal axis. Strand surface 134 may include any number of grooves 178 and 180. In embodiments, grooves 178 and 180 are embedded in strand surface 134 and may be 0.01 millimeters deep. Grooves 178 and 180 may be positioned along the outer surface 134 of strand 176 in various positions. For example, grooves 178 and 180 may be positioned lengthwise along the longitudinal axis of the body of strand 176. In other embodiments, grooves 178 and 180 may be rotationally embedded in strand surface 134. Still further examples include intersecting grooves 178 and 180. Strand 176 may be capable of being dispensed from needle body 102 of an implant needle 100, as depicted in FIGS. 1 and 2.

Figure 12:
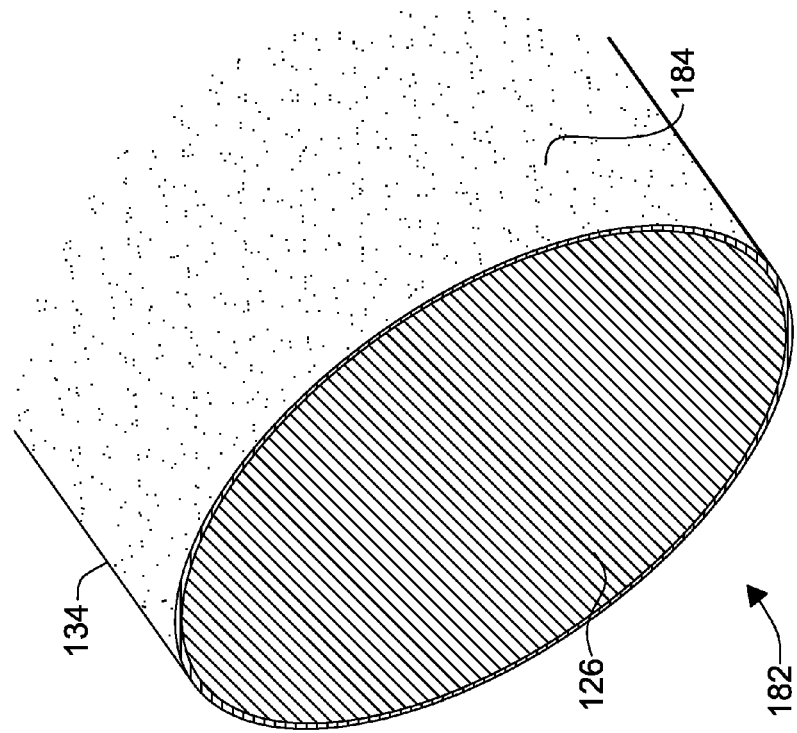

Referring next to FIG. 12, an illustrative cross-sectional view of rough bio-absorbable strand 182 is shown. FIG. 12 illustrates strand surface 134, surface texture 184, and seed 126. The body of strand 182 is cylindrical in shape and positioned along a longitudinal axis. Surface texture 184 may be created in a variety of ways. For instance, surface texture 184 may result from small indentations on strand surface 134. In other embodiments, surface texture 184 may be granular pieces of bio-absorbable material dispersed along strand surface 134. It should be understood that strand surface 134 may include other variations which create a rough surface, in addition to the rough surface created with surface texture 184. For example, strand surface 134 may also include prongs, ridges, strips, grooves, or the like. Strand 182 may be capable of being dispensed from needle body 102 of an implant needle 100, as depicted in FIGS. 1 and 2.

Figure 13:
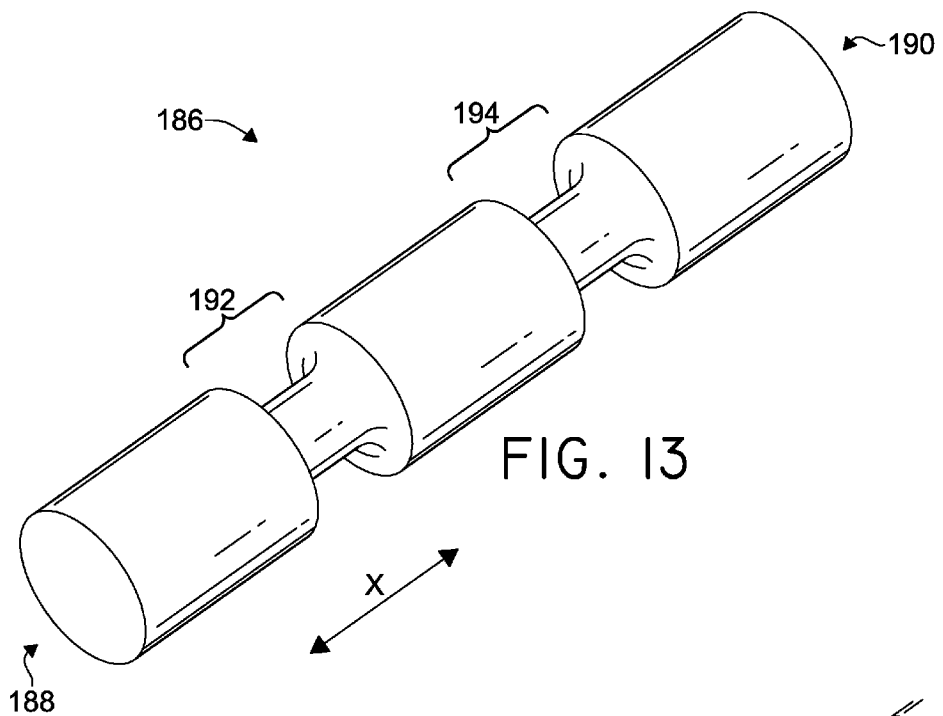
FIG. 13 is a perspective view of a spacer constructed in accordance with an embodiment of the invention.

With reference now to FIG. 13, an exemplary spacer 186 is shown for embedding within a rough, bio-absorbable strand. Spacer 186 is generally cylindrical in shape along a central, longitudinal axis "x." Spacer 186 includes axially opposed first and second ends. Proximal first end 188 and distal second end 190 are closed. In embodiments, spacer 186 has an approximate diameter within the range of about 0.23 to 2.68 millimeters, and an approximate length within the range of about 10 to 150 millimeters. In one embodiment, a spacer has an inner diameter of about 0.8 millimeters and an approximate length of about 4.5 millimeters. Spacer 186 includes areas 192 and 194 where deep grooves are embedded in spacer 186. As such, spacer 186, when embedded in a bio-absorbable strand, may help prevent the bio-absorbable strand from sliding and shifting position. It should be understood that the number of spacers may vary between different strands of rough, bio-absorbable material depending on the intended patient for which the strand is created. It should also be understood that areas 192 and 194 may vary in depth and width along spacer 186.

Figure 14:
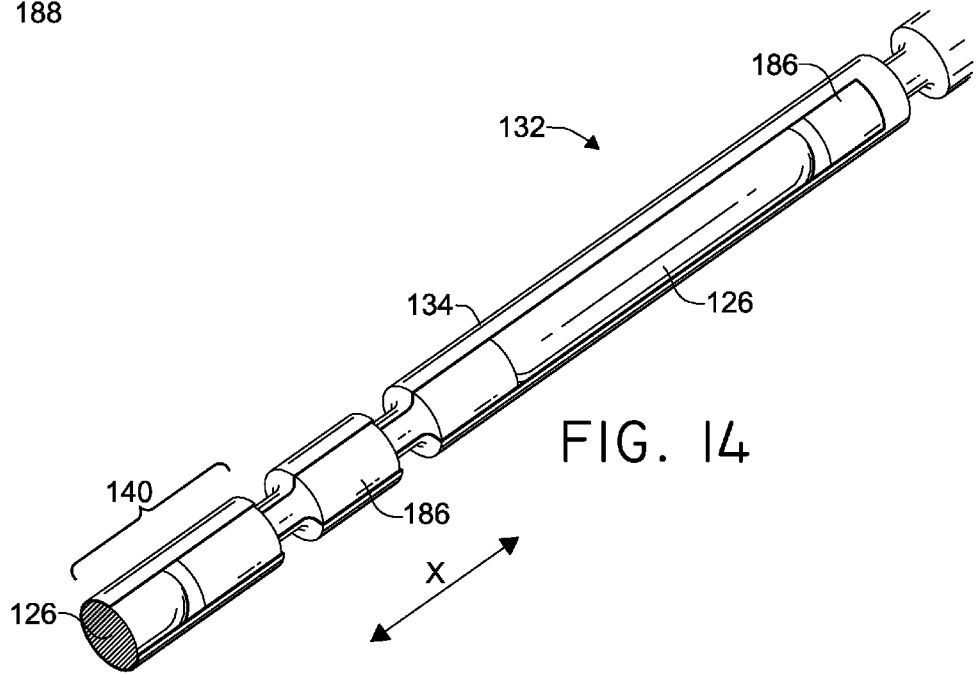
FIG. 14 is a is a perspective view of a bio-absorbable strand constructed in accordance with an embodiment of the invention with a portion of the strand removed to expose seeds and spacers embedded in the body of the strand.

Referring finally to FIG. 14, an illustrative rough bio-absorbable strand 132 used for seed placement is shown. As shown in FIG. 14, strand 132 generally includes outer surface 134, radioactive seed 126, and spacer 186. Strand 132 also includes area 140 depicting a cut away portion of outer surface 134, which reveals the contents inside strand 132. The body of strand 132 is generally cylindrical in shape and is positioned along a central, longitudinal axis "x." It should be understood that the cylindrical shape of strand 132 may vary between embodiments, and that the shape of strand 132 is such that at least one seed 126 may be embedded inside or contained within hollow strand 132. Strand surface 134 is shown conforming to the grooves in spacer 186. In embodiments, strand surface 134 conforming to the grooves of spacer 186 helps prevent bio-absorbable strand 132 from sliding and shifting inside a patient. In embodiments, more than one spacer 186 is used to separate more than one seed 126. For instance, two radioactive seeds may be separated by five spacers. In embodiments, spacer 186 may be made of the same bio-absorbable material as the outer surface 134 of strand 132. In other instances, spacer 186 may be a different bio-absorbable material than strand 132 or may be natural or synthetic materials.

In embodiments, strand 132 has an inner diameter of about 0.838 millimeters when used in an 18-guage needle. In other embodiments, strand 132 has an inner diameter in the range of about 0.241 to 2.691 millimeters for a needle between about 26-guage to 10-guage, respectively. As explained with reference to FIG. 3, seed 126 may have a diameter of about 0.8 millimeters. In embodiments, the inner diameter of seed 126 is within the range of about 0.23 to 2.68 millimeters. Therefore, the bio-absorbable material of strand 132 surrounding seed 126 may have a thickness of about 0.019 millimeters. In further embodiments, spacer 186 may have the same or different diameter as seed 126. For example, spacers 186 may be about 0.8 millimeters thick. In embodiments, bio-absorbable strand 132 is capable of being dispensed from an implant needle 100 with an inner diameter of 0.838 millimeters in needle body 102, as depicted in FIGS. 1 and 2.

As can be understood, embodiments of the present invention relate to a rough, bio-absorbable strand for securing the placement of radioactive seeds in a patient. The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated by and is within the scope of the claims.

What is claimed is:

1. A bio-absorbable strand for securing the placement of radioactive seeds inside a patient, the strand comprising:
   an elongated body of bio-absorbable material, wherein the elongated body of the strand is positioned along a central longitudinal axis, the elongated body having one or more raised strips of bio-absorbable material of additional thickness rotationally positioned along the strand surface in a corkscrew manner, wherein the one or more raised strips of bio-absorbable material are at least partially connected to the strand surface such that parts of the one or more raised strips split off of the strand surface, projecting outward from the central longitudinal axis of the strand;
   a plurality of radioactive seeds imbedded in the body of the strand; and
   one or more bio-absorbable spacers imbedded between the plurality of radioactive seeds.

2. The strand of claim 1, further comprising a plurality of sets of alternating pairs of prongs facing alternating directions within each of the plurality of sets, each of said plurality of sets of alternating pairs of prongs projecting from the bio-absorbable material of the strand's outer surface along the central longitudinal axis of the elongated body, wherein the plurality of sets of alternating pairs of prongs have the capability to move from a depressed position along the outer surface of the strand, to an extended position projecting from the outer surface of the strand, wherein the plurality of sets of pairs of prongs are in the depressed position when enclosed inside an implant needle and are in the extended position when dispensed from the implant needle and wherein the prongs are bio-absorbable.

3. The strand of claim 1, wherein the one or more raised strips of bio-absorbable material overlap and extend along the central longitudinal axis of the body of the strand.

4. The strand of claim 1, wherein the one or more raised strips of bio-absorbable material are a continuous part of the strand.

5. The strand of claim 1, wherein the one or more raised strips of bio-absorbable material are comprised of additional attached layers on top of the surface of the strand.

6. The strand of claim 1, wherein the one or more raised strips of bio-absorbable material are comprised of the same bio-absorbable material as the strand.

7. The strand of claim 1, wherein the one or more raised strips of bio-absorbable material projecting from the strand surface where not fully connected remain depressed along the surface of the strand in a depressed position when enclosed in a needle body of an implant needle and project from the strand surface in an extended position when dispensed from the implant needle, securing the strand inside a patient.

8. A rough bio-absorbable strand for securing the placement of radioactive seeds inside a tissue of a patient, the strand comprising:
   a central body of bio-absorbable material, wherein the central body is an elongated strand of bio-absorbable material having a central longitudinal axis;
   a rough outer surface of the central body, wherein the rough outer surface comprises one or more raised ridges of bio-absorbable material of additional thickness, each of the one or more raised ridges rotationally positioned on the strand surface extending lengthwise along the central longitudinal axis in a corkscrew manner from a proximal first end to a distal second end along the central body, wherein the one or more raised ridges are configured to secure the placement of the bio-absorbable structure inside the tissue of a patient; and a plurality of active elements implanted in the central body of the bio-absorbable structure, wherein the plurality of active elements contain therapeutic properties for treatment of a patient.

9. The bio-absorbable structure of claim 8, wherein the one or more raised ridges of bio-absorbable material are capable of securing the placement of the bio-absorbable structure inside the tissue of the patient, wherein the rough outer surface extends along the central longitudinal axis of the central body, and further wherein the rough outer surface comprises a plurality of sets of alternating pairs of prongs facing alternating directions that project from the structure's outer surface and have the capability to move from a depressed position along the outer surface of the structure when enclosed inside an implant needle, to an extended position projecting from the outer surface of the structure when dispensed from the implant needle; and wherein the plurality of sets of alternating pairs of prongs comprises at least two sets of alternating pairs of prongs positioned along the rough outer surface, wherein each of the at least two sets of alternating pairs of prongs comprises a first prong adjacent a second prong, wherein the first prong and the second prong are positioned in alternating directions such that the first prong and the second prong open to an extended position facing in opposite directions from each other, wherein the at least two sets of alternating pairs of prongs are positioned along the central longitudinal axis to prevent shifting or movement of the strand from an original position of the strand.

10. The rough bio-absorbable structure of claim 9, further comprising one or more bio-absorbable spacers implanted between two or more of the one or more active elements, wherein at least one of the one or more bio-absorbable spacers comprises one or more deep grooves embedded in an outer surface of the at least one of the one or more bio-absorbable spacers.

11. The rough bio-absorbable structure of claim 8, further comprising one or more grooves embedded in the strand surface in a rotational manner.

12. The rough bio-absorbable structure of claim 11, wherein the one or more grooves intersect with the one or more raised ridges.

13. The rough bio-absorbable structure of claim 8, wherein the one or more raised ridges of bio-absorbable material are 0.1 millimeters thick.

14. A rough bio-absorbable strand for securing the placement of radioactive seeds inside a tissue of a patient, the strand comprising:

a central body of bio-absorbable material, wherein the central body is an elongated strand of bio-absorbable material having a central longitudinal axis;

a rough outer surface of the central body, wherein the rough outer surface comprises one or more raised ridges of bio-absorbable material of additional thickness rotationally positioned on the strand surface along the central longitudinal axis in a corkscrew manner, wherein the one or more raised ridges are configured to secure the placement of the bio-absorbable structure inside the tissue of a patient, and wherein the one or more raised ridges of bio-absorbable material comprise at least two ridges that overlap at one or more points along the central longitudinal axis of the body of the strand, further adding thickness to the strand; and a plurality of active elements implanted in the central body of the bio-absorbable structure, wherein the plurality of active elements contain therapeutic properties for treatment of a patient.

15. The rough bio-absorbable structure of claim 14, wherein the ridges are partially attached to the strand body such that the unsecured portions of the ridges extend outward from the body of the strand.

* * * * *